United States Patent [19]

Samano et al.

[11] Patent Number: 6,143,748
[45] Date of Patent: Nov. 7, 2000

[54] PROCESS FOR SYNTHESIS OF NUCLEOSIDE ANALOGUES

[75] Inventors: Mirna C. Samano; Vicente Samano, both of ChapelHill, N.C.; Michael David Goodyear, Ware, United Kingdom

[73] Assignee: Glaxo Wellcome Inc., Research Triangle Park, N.C.

[21] Appl. No.: 08/930,224

[22] PCT Filed: Mar. 26, 1996

[86] PCT No.: PCT/EP96/01353

§ 371 Date: Sep. 30, 1997

§ 102(e) Date: Sep. 30, 1997

[87] PCT Pub. No.: WO96/30369

PCT Pub. Date: Oct. 3, 1996

[30] Foreign Application Priority Data

Mar. 31, 1995 [GB] United Kingdom .................. 9506644

[51] Int. Cl.⁷ ....................... C07D 411/04; A61K 31/505
[52] U.S. Cl. .............................. 514/256; 514/49; 514/50; 514/274; 536/4.1; 544/242; 544/245; 544/253; 544/255; 544/285; 544/293

[58] Field of Search ..................................... 514/256, 274, 514/49, 50; 536/4.1; 436/19; 544/242, 245, 253, 255, 285, 293

[56] References Cited

U.S. PATENT DOCUMENTS 5,538,975   7/1996   Dionne ..................................... 514/256

OTHER PUBLICATIONS

Jung, M.E. et al., New Approach to the Synthesis of β–2'–Deoxyribonucleosides; Intramolecular Vorbrüggen Coupling, *Journal of Organic Chemistry*, vol. 58, pp. 807–808, 1993.

*Primary Examiner*—James O. Wilson
*Assistant Examiner*—Howard Owens
*Attorney, Agent, or Firm*—Nixon & Vanderhye

[57] ABSTRACT

The present invention is concerned with a process for the preparation of antiviral 1,3-oxathiolane nucleosides comprising an intramolecular glycosylation reaction to produce exclusively the β-diastereomer, and intermediates useful in the process.

15 Claims, No Drawings

PROCESS FOR SYNTHESIS OF NUCLEOSIDE ANALOGUES

This application is filed pursuant to 35 U.S.C. § 371 as a U.S. National Phase Application of International Application No. PCT/EP96/01353 filed Mar. 26, 1996 which claims priority from GB9506644.5 filed Mar. 31, 1995.

The present invention is concerned with a process for the preparation of anti-viral 1,3-oxathiolane nucleosides, which employs an intramolecular glycosylation to produce exclusively the β-diastereomer. The invention also relates to novel intermediates obtained by the process.

1,3-Oxathiolane nucleosides possess two chiral centres (at the C1'- and C4'-positions according to the furanose numbering system) and typically exist as diastereomeric pairs of the α- and β-forms, each form comprising two enantiomers. The α- and β-diastereoisomers tend to have different anti-viral activities, the β-form typically being the more potent. Similarly, the enantiomeric pairs of each diastereomer tend to have different properties.

β-Diastereomers have traditionally been obtained by preparation of the diastereomeric mixture followed by laborious separation of the β-form by physical means such as differential solubility or chromatography. It follows that the overall yield of β-isomer is typically less than 50%.

International Patent Application No. WO91/11186 (U.S. Pat. No. 5,204,466) describes a process whereby 1,3-oxathiolane nucleosides may be obtained with high β-diastereoselectivity by condensing a carbohydrate or carbohydrate-like moiety with a heterocyclic base in the presence of a specific Lewis acid, typically stannic chloride. The process is further exemplified in International Patent Application No. WO92/14743.

Further diastereoselective processes for the preparation of nucleoside analogues involving condensation of a carbohydrate or like moiety with a purine or pyrimidine base are described in WO92/20669 (U.S. Pat. No. 5,756,706) and WO95/29174.

We have now developed an efficient new process which provides exclusively the β-diastereomer of a 1,3-oxathiolane pyrimidine nucleoside with no α-contamination. The critical steps involved in the synthesis are cyclisation of an appropriate heterocyclic acetaldehyde with 1,4-dithiane-2,5-diol to give a "5'-tethered" 1,3-oxathiolane nucleoside analogue which then undergoes an intramolecular glycosylation on the same face of the carbohydrate ring to give exclusively the (1'-tethered) β-diastereomer. The intramolecular glycosylation of 5'-tethered furanose nucleosides is known from, inter alia, Japanese Patent No. 06263792-A, but the prior art comprises no reports of applying such methodology to the preparation of anti-viral 1,3-oxathiolane nucleosides. The resulting β-diastereomer may be hydrolysed to the corresponding cytidine analogue or may be resolved by any suitable technique known to a skilled person, for example, by esterification followed by selective enzymatic hydrolysis, removal of the 'unwanted' enantiomer and hydrolysis of the ester of desired enantiomeric configuration. Alternatively, it may be possible, for example, by use of a chiral auxiliary, to obtain intermediates substantially enantiomerically pure which intermediates can be carried forward to yield the desired enantiomerically pure product.

According to one aspect of the present invention, there is provided a process for the preparation of compounds of formula (I)

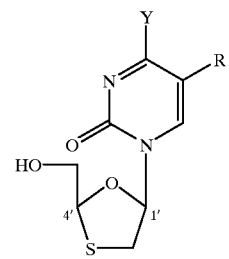

wherein R is hydrogen, $C_{1-6}$ alkyl, or halogen and Y is hydroxy, amino, $C_{1-6}$ alkoxy or $OR^1$, where $R^1$ is a chiral auxiliary, which process comprises treating a compound of formula (II)

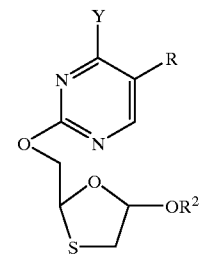

wherein R and Y are as hereinbefore defined and $R^2$ represents hydrogen, $C_{1-6}$acyl, $C_{1-6}$alkyl or halogen with a suitable Lewis acid or a reagent apt to convert the group $OR^2$ to a leaving group.

Suitable Lewis acids include, for example, stannic chloride or trimethylsilyl triflate. Reaction with a Lewis acid is suitably conducted at reduced temperature (e.g. 0° C. to −20° C.) in a polar aprotic solvent followed by treatment with base.

Where $R^2$ is H, the group $OR^2$ may conveniently be converted to a leaving group by reaction with a halogenating agent such as a thionyl halide or an oxalyl halide, or a tosyl or mesyl halide. Other methods for converting $OR^2$ to a leaving group (i.e. a group which can be readily displaced by the ring nitrogen atom) will be apparent to those skilled in the art.

It is to be understood that where the variable R occurs more than once in a general formula, it may represent the same group at each position, or different groups.

As used herein halogen means bromine, chlorine, fluorine or iodine, especially chlorine or fluorine, more especially fluorine.

The term "chiral auxiliary" describes an asymmetric molecule that is used to effect the chemical resolution of a racemic mixture. Such chiral auxilliaries may possess one chiral centre such as α-methylbenzylamine or several chiral centres such as menthol. The purpose of the chiral auxiliary, once built into the starting material, is to allow simple separation of the resulting diastereomeric mixture. See, for example, J Jacques et al., *Enantiomers, Racemates and Resolutions*, pp. 251–369, John Wiley & Sons, New York (1981).

Where $R^1$ represents a chiral auxiliary it will preferably be selected from (d)-menthyl, (l)-menthyl, (d)-8-phenylmenthyl, (l)-8-phenylmenthyl, (+)-norephedrine and (−)-norephedrine. More preferably $R^1$ is (l)-menthyl, or (d)-menthyl, most preferably (l)-menthyl.

According to a further aspect, the present invention provides a process for the preparation of a compound of formula (Ia)

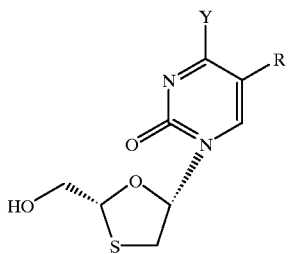
(Ia)

wherein R and Y are as previously defined, which process comprises treating a compound of formula (IIa)

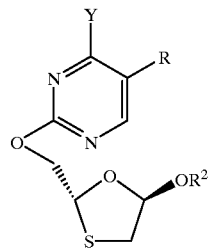
(IIa)

wherein R, Y and $R^2$ are as previously defined with a suitable Lewis acid or a reagent apt to convert the group $OR^2$ to a leaving group.

According to another aspect of the invention, there is provided a process for the preparation of compounds of formula (II) which comprises reacting a compound of formula (III)

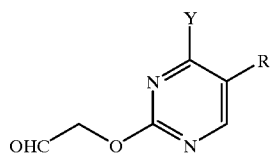
(III)

wherein R and Y are as hereinbefore defined, with 1,4-dithiane-2,5-diol at elevated temperature (e.g. 100° C.) in a non-polar aprotic solvent to give a compound of formula (II) wherein $R^2$ is H. Compounds of formula (II) wherein $R^2$ is other than H may be prepared from the corresponding hydroxy compound by derivatisation using any standard procedure, for example, treatment with alkanoyl halide/base or carboxylic anhydride/base.

Reaction of a compound of formula (III) with 1,4-dithiane-2,5-diol results in a mixture of isomers of the compounds of formula (II) wherein $R^2$ is H. Where Y is $OR^1$, the compounds of formula (IIa) may be selectively crystalized from the diastereomeric mixture. In a further or alternative aspect, the present invention accordingly provides a method for obtaining the compound of formula (IIa) wherein R is H and Y is $OR^1$ from a mixture of isomers by treatment of the mixture of isomers, at least partially in solution, with an agent capable of effecting interconversion of the isomers without complete suppression of the crystallisation of the desired single enantiomer (IIa) wherein R is H and Y is $OR^1$. Other compounds of formula (IIa) may be prepared from compounds of formula (IIa) wherein R is H and Y is $OR^1$ by conventional methods.

Agents capable of effecting interconversion of the isomers without complete suppression of the crystallisation of the trans isomers include, for example, alcohols, such as, for example, methanol, ethanol, n-propanol, i-propanol, n-butanol, i-butanol, t-butanol, and organic bases, in particular tertiary amines, for example, pyridine and triethylamine and Hunig's base. A preferred agent is triethylamine.

The interconversion of isomers may be effected in any suitable solvent or mixture of solvents which does not otherwise react with the alcohols of formula (II), under conditions of concentration and temperature which permit crystallisation of the desired isomer or isomers and which do not cause significant degradation of the desired isomer or isomers. Suitable solvents may include for example, aliphatic or aromatic hydrocarbons, ethers, esters and chlorinated hydrocarbons. The interconversion will preferably be effected at a temperature of about −20° to 120° C., more preferably in the range of about −10° to 80° C., such as about 0° to 50° C.

It will be appreciated by those skilled in the art that selection of solvent, temperature, interconversion agent and, particularly, the quantity of the interconversion agent is best conducted as an integrated exercise dependent on the nature of the groups R, $R^1$ and $R^2$ present in the isomers. However, when an organic base is used as the interconversion agent, the preferred quantity is generally less than two mole-equivalents based on the total of all isomers of (II) present.

The interconversion of isomers may be conducted separately from the preparation of the isomeric mixture; however, it is conveniently conducted concomitantly with that preparation.

The interconversion procedure may also be used to increase the isomeric purity of isolated (IIa).

By means of the interconversion process, the isolated yield of the desired isomer (IIa) may be enhanced to greater than 50% of theory (based on formation of all stereoisomers), typically to between about 60% and about 90% of theory; but it is not ruled out that yields approaching 100% of theory may be obtained.

Compounds of formula (III) may be prepared by reacting a compound of formula (IV)

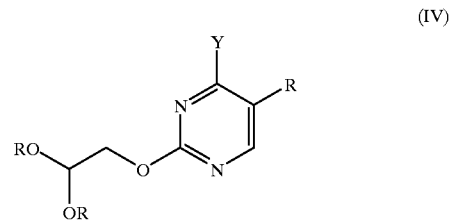
(IV)

wherein R (which may be the same or different) and Y are as hereinbefore defined, with aqueous trifluoroacetic acid (90%) at elevated temperature.

Compounds of formula (IV) may be prepared by reacting a compound of formula (V)

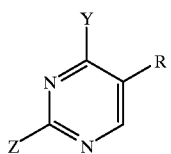

(V)

wherein R and Y are as hereinbefore defined and Z is a suitable leaving group, for example, chlorine, with a compound of formula (VI)

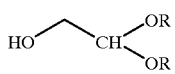

(VI)

wherein R (which may be the same or different) are as hereinbefore defined, at reduced temperature in a polar aprotic solvent in the presence of base.

Compounds of formula (V) may be prepared by reacting a compound of formula (VII)

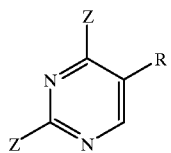

(VII)

wherein R and Z (which may be the same or different) are as hereinbefore defined, with a suitable nucleophile, for example, in the case where Y in the compound of formula (V) is to be ethoxy, EtO⁻ (NaOEt/EtOH).

Compounds of formulae (VI) and (VII) may be obtained commercially or prepared from commercially available starting materials by methods known to a skilled person, for example, in the case where R in the compound of formula (VII) is to be fluorine and Z chlorine, by treating 5-fluorouracil with phosphorus oxychloride at elevated temperature in the presence of base.

As indicated, compounds of formula (I) wherein Y at the C4-position is $C_{1-6}$ alkoxy or $OR^1$ may be converted to a cytidine analogue ($Y=NH_2$) by heating with ammoniacal methanol or, where racemic, may be resolved by any suitable technique known to a skilled person, for example, by one of the enzyme procedures described in International Patent No. WO92/14743.

According to such a procedure, the racemic β-diastereomer (I) is esterified at the C5'-position using, for example, butyric anhydride, and the racemic ester (VIII) is treated with a suitable enzyme, typically pig liver esterase, to preferentially hydrolyse the 'unwanted' enantiomer back to the 5'-OH compound (IX) which is water-soluble and can be separated from the desired (unhydrolysed) enantiomer (X). The latter is converted to the 4-$NH_2$, 5'-OH compound of desired enantiomeric configuration by heating with ammoniacal methanol.

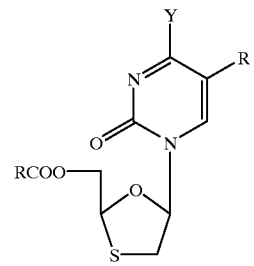

(VIII)

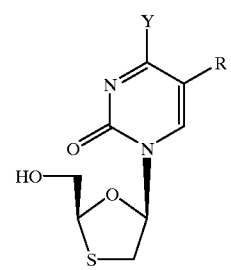

(IX)

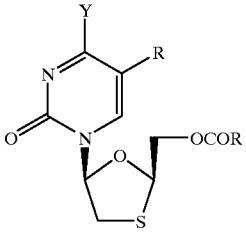

(X)

The process of the invention finds particular application in the preparation of (2R,5S)-5-fluoro-1-[2-(hydroxymethyl)-1,3-oxathiolan-5-yl]cytosine, (2R,5S)-1-[2-(hydroxymethyl)-1,3-oxathiolan-5-yl]cytosine, (±)-cis-5-fluoro-1-[2-(hydroxymethyl)-1,3-oxathiolan-5-yl]-cytosine and (±)-cis-1-[2-(hydroxymethyl)-1,3-oxathiolan-5-yl] cytosine.

According to a further aspect of the invention, there are provided novel compounds of formulae (IV), (III), (II) and (I) (which latter includes the racemate, the (2S,5R)-enantiomer (IX), the esterified racemate (VIII) and the esterified (2R,5S)-enantiomer (X)). Specific intermediate compounds arising from the preparation of (2R,5S)-5-fluoro-1-[2-(hydroxymethyl)-1,3-oxathiolan-5-yl]cytosine, (2R,5S)-1-[2-(hydroxymethyl)-1,3-oxathiolan-5-yl] cytosine, (±)-cis-5-fluoro-1-[2-(hydroxymethyl)-1,3-oxathiolan-5-yl]-cytosine and (±)-cis-1-[2-(hydroxymethyl)-1,3-oxathiolan-5-yl]cytosine include:

2-(2,2-Dimethoxyethoxy)-4-ethoxy-5-fluoropyrimidine
2-(2,2-Dimethoxyethoxy)-4-ethoxypyrimidine
2-[(4-Ethoxy-5-fluoro-2-pyrimidinyl)oxy]acetaldehyde
2-[(4-Ethoxy-2-pyrimidinyl)oxy]acetaldehyde
2-{[(4-Ethoxy-5-fluoro-2-pyrimidinyl)oxy]methyl}-1,3-oxathiolan-5-ol
2-{[(4-Ethoxy-2-pyrimidinyl)oxy]methyl}-1,3-oxathiolan-5-ol
2-{[(4-Ethoxy-5-fluoro-2-pyrimidinyl)oxy]methyl}-1,3-oxathiolan-5-yl acetate
2-{[(4-Ethoxy-2-pyrimidinyl)oxy]methyl}-1,3-oxathiolan-5-yl acetate
(2S*,5R*)-4-Ethoxy-5-fluoro-1-[2-(hydroxymethyl)-1,3-oxathiolan-5-yl]pyrimidin-2-one
(2S*,5R*)-4-Ethoxy-1-[2-(hydroxymethyl)-1,3-oxathiolan-5-yl]pyrimidin-2-one (2S*,5R*)-4-Ethoxy-5-fluoro-1-[2-(butanoyloxymethyl)-1,3-oxathiolan-5-yl]pyrimidin-2-one
(2S*,5R*)-4-Ethoxy-1-[2-(butanoyloxymethyl)-1,3-oxathiolan-5-yl]pyrimidin-2-one
(2S,5R)-4-Ethoxy-5-fluoro-1-[2-(hydroxymethyl)-1,3-oxathiolan-5-yl]pyrimidin-2-one
(2S,5R)-4-Ethoxy-1-[2-(hydroxymethyl)-1,3-oxathiolan-5-yl]pyrimidin-2-one
(2R,5S)-4-Ethoxy-5-fluoro-1-[2-(butanoyloxymethyl)-1,3-oxathiolan-5-yl]pyrimidin-2-one
(2R,5S)-4-Ethoxy-1-[2-(butanoyloxymethyl)-1,3-oxathiolan-5-yl]pyrimidin-2-one The following examples of the process of the invention are for illustration only and are not intended to limit the scope of the invention in any way. In all cases, $^1$H NMR and C,H,N elemental analysis were consistent with the proposed structure.

EXAMPLE 1

Preparation of (2R,5S)-5-fluoro-1-[2-(hydroxymethyl)-1,3-oxathiolan-5-yl]cytosine (a) 2,4-Dichloro-5-fluoropyrimidine To a suspension of 5-fluorouracil (Aldrich, 8.00 g, 61.5 mmol) in phosphorus oxychloride (25.0 mL, 41.12 g, 268 mmol) was added N,N-diethylaniline (12.6 mL, 11.81 g, 80 mmol) and the mixture was heated at 100° C. for 1.5 hours. Solvent was evaporated in vacuo and the residue poured into cold H$_2$O/Et$_2$O (400 mL, 1:1). The aqueous phase was extracted with Et$_2$O and the combined organic phase was dried (Na$_2$SO$_4$) and evaporated (water aspirator pump, 35° C.) to give the desired product (10.2 g, 99%) as a yellowish solid: mp 34–36° C. (lit. 35–36° C.).

(b) 2-Chloro-4-ethoxy-5-fluoropyrimidine

To a solution of the product from step (a) (10.0 g, 59.9 mmol) in abs. EtOH (40 mL) at 0° C. under nitrogen atmosphere was added 1M NaOEt/EtOH (61 mL, 61 mmol) and the mixture was stirred for 1 hour. Solvent was evaporated in vacuo and the residue partitioned between H$_2$O and Et$_2$O. The aqueous phase was extracted with Et$_2$O and the combined organic phase was washed with brine, dried (Na$_2$SO$_4$) and evaporated (water aspirator pump, 35° C.) to provide the desired product (8.74 g, 83%) as a yellowish solid: mp 30–32° C. (lit. 31–32° C.); $^1$H NMR (CDCl$_3$): δ1.46 (t, J=7.0 Hz, 3H), 4.53 (quartet, J=7 Hz, 2H), 8.17 (d, J=2.1 Hz, 1H); MS m/z 179 (M+3, 17%), 177 (M+1, 50%), 149 (100%). Anal. Calcd. for C$_6$H$_6$ClFN$_2$O: C, 40.81; H, 3.42; N, 15.86. Found, C, 40.90; H, 3.45; N, 15.81.

(c) 2-(2,2-Dimethoxyethoxy)-4-ethoxy-5-fluoropyrimidine

To a suspension of 60% NaH/mineral oil (2.88 g, 72.2 mmol) in anhydrous DMF (70 mL) at 0° C. under nitrogen atmosphere was slowly added glycolaldehyde dimethyl acetal (Lancaster, 6.13 g, 57.7 mmol). The mixture was stirred at ambient temperature for 1 hour and then transferred to a solution of the product from step (b) (8.5 g, 48.1 mmol) in anhydrous DMF (70 mL) at −55° C. over 15 minutes. The mixture was allowed to warm to −20° C. over 2 hours and then neutralized with AcOH. Solvent was evaporated in vacuo and the residue partitioned between H$_2$O and CH$_2$Cl$_2$. The aqueous phase was extracted with CH$_2$Cl$_2$ and the combined organic phase was dried (Na$_2$SO$_4$) and evaporated. The residue was flash chromatographed (EtOAc/hexanes, 1:5) to give the desired product (9.75 g, 82%) as an oil: $^1$H NMR (CDCl$_3$): δ1.42 (t, J=7.0 Hz, 3H), 3.43 (s, 6H), 4.32 (d, J=5.2 Hz, 2H), 4.50 (quartet, J=7.0 Hz, 2H), 4.75 (t, J=5.2 Hz, 1H), 8.03 (d, J=2.4 Hz, 1H); MS m/z 215 (M-OCH$_3$, 100%). Anal. Calcd. for C$_{10}$H$_{15}$FN$_2$O$_4$: C, 48.78; H, 6.14; N, 11.38. Found: C, 48.84; H, 6.06; N, 11.36.

(d) 2-[(4-Ethoxy-5-fluoro-2-pyrimidinyl)oxy]acetaldehyde

A mixture of the product from step (c) (6.0 g, 24.4 mmol) and 90% TFA/H$_2$O (50 ml) was heated at 50° C. for 2.5 hours. Solvent was evaporated in vacuo and the residue partitioned between CHCl$_3$ and saturated NaHCO$_3$/H$_2$O. The aqueous phase was extracted with CHCl$_3$ (×2) and the combined extracts dried (Na$_2$SO$_4$) and evaporated to give the desired product (4.82 g, 99%) as a colourless oil which was used in the next step without further purification. Flash chromatography (EtOAc/hexanes, 1:2) gave analytically pure material as a colourless oil: $^1$H NMR (CDCl$_3$): δ1.43 (t, J=7.0 Hz, 3H), 4.40 (quartet, J=7.0 Hz, 2H), 4.81 (s, 2H), 8.03 (d, J=1.8 Hz, 1H), 9.74 (s, 1H); MS m/z 201 (M+1, 100%). Anal. Calcd. for C$_8$H$_9$FN$_2$O$_3$.0.25 H$_2$O: C, 46.95; H, 4.68; N, 13.69. Found: C, 46.81; H, 4.61; N, 13.64.

(e) 2-{[(4-Ethoxy-5-fluoro-2-pyrimidinyl)oxy]methyl}-1,3-oxathiolan-5-ol

A mixture of the product from step (d) (4.6 g, 23.0 mmol) and 1,4-dithiane-2,5-diol (Aldrich, 1.92 g, 12.65 mmol) in anhydrous toluene (90 mL) was heated at 100° C. for 2 hours. The mixture was filtered and the filtrate was concentrated and dried in vacuo to give the desired product (6.27 g, 99%) as a waxy pale yellow solid which was used in the next step without further purification (~1:1 diastereomeric ratio by $^1$H NMR spectroscopy). Flash chromatography (EtOAc/hexanes, 1:2) afforded analytically pure material as a white solid: mp 85–87° C.; $^1$H NMR (CDCl$_3$): δ1.41 (t, J=7.0 Hz, 3H), 2.42 (br s, 1H), 3.10 (d, J=11.0 Hz, 1H), 3.20 (dd, J=11.0, 3.5 Hz, 1H), 4.40 (dd, J=12.0, 3.5 Hz, 1H), 4.43 (quartet, J=7.0 Hz, 2H), 4.77 (dd, J=12.0, 7.0 Hz, 1H), 5.70 (dd, J=7.0. 3.5 Hz, 2H), 5.92 (d, J=3.5 Hz, 1H), 8.04 (d, J=2.5 Hz, 1H); a similar set of signals appeared for the other diastereomer; MS m/z 201 (M-C$_2$H$_3$OS, 100%). Anal. Calcd. for C$_{10}$H$_{13}$FN$_2$O$_4$S: C, 43.47; H, 4.74; N, 10.14; S, 11.61. Found: C, 43.56; H, 4.78; N, 10.04; 11.66.

(f) 2-{[(4-Ethoxy-5-fluoro-2-pyrimidinyl)oxy]methyl}-1,3-oxathiolan-5-yl acetate To a solution of the product from step (e) (1.0 g, 3.62 mmol) and pyridine (0.8 mL, 0.78 g, 9.88 mmol) in CH$_2$Cl$_2$ (12 mL) at 0° C. was added AcCl (0.35 mL, 0.37 g, 4.7 mmol). After 1 hour at ambient temperature, saturated NaHCO$_3$/H$_2$O was added and the aqueous phase was extracted with CHCl$_3$. The combined organic phase was washed with brine, dried (Na$_2$SO$_4$), evaporated and dried in vacuo to give the desired product (1.13 g, 99%) as a yellow oil which was used in the next step without further purification (~2:1 diastereomeric ratio by $^1$H NMR spectroscopy). Flash chromatography (acetone/CH$_2$Cl$_2$, 1:24) gave analytically pure material as a colourless oil: $^1$H NMR (CDCl$_3$): δ1.42 (t, J=7.0 Hz, 3H), 2.07 (s, 3H), 3.15 (d, J=11.5 Hz, 1H), 3.38 (dd, J=11.5, 4.0 Hz, 1H), 4.40–4.60 (m, 4H), 5.73 (m, 1H), 6.70 (d, J=4.0 Hz, 1H), 8.03 (d, J=2.5 Hz, 1H); a similar set of signals appeared for the minor diastereomer; MS m/z 259 (M-OAc, 9%), 159 (100%). Anal. Calcd. for C$_{12}$H$_{15}$FN$_2$O$_5$S: C, 45.28; H, 4.75; N, 8.80; S, 10.07. Found: C, 45.35; H. 4.76; N, 8.83; S, 10.11.

(g) (2S*,5R*)-4-Ethoxy-5-fluoro-1-[2-(hydroxymethyl)-1,3-oxathiolan-5-yl]pyrimidin-2-one To a mixture of the product from step (f) (0.21 g, 0.66 mmol) and 4 Å molecular sieves (0.3 g) in anhydrous CH$_3$CN (20 mL) at −20° C. under nitrogen atmosphere was slowly added trimethylsilyl triflate (Aldrich, 0.14 mL, 0.16 g, 0.73 mmol). After stirring the mixture for 2 hours at −20° C., 1M NaOH/H$_2$O (2.0 mL, 2.0 mmol) was added. After 2 hours at 0° C., the mixture was neutralized with AcOH. Solvent was evaporated in vacuo and the residue flash chromatographed (EtOAc/hexanes, 9:1) to give the desired product (0.11 g, 60%) as a white solid: mp 162–164° C.; $^1$H NMR (DMSO-d$_6$): δ1.39 (t, J=7.0 Hz, 3H), 3.29 (dd, J=12.0, 2.7 Hz, 1H), 3.60 (dd, J=12.0, 5.4 Hz, 1H), 3.82 (ddd, J=12.5, 5.4, 3.5 Hz, 1H), 3.95 (ddd, J=12.5, 5.4, 3.5 Hz, 1H), 4.45 (quartet, J=7.0 Hz, 2H), 5.31 (t, J=3.5 Hz, 1H), 5.63 (t, J=5.4 Hz, 1H), 6.20 (m, 1H), 8.74 (d, J=6.7 Hz, 1H); MS m/z 277 (M+1, 4%), 159 (100%). Anal. Calcd. for C$_{10}$H$_{13}$FN$_2$O$_4$S: C, 43.47; H, 4.74; N, 10.14; S, 11.61. Found: C, 43.54; H, 4.76; N, 10.18; S, 11.52.

(h) (2S,5R*)-4-Ethoxy-5-fluoro-1-[2-(butanoyloxymethyl)-1,3-oxathiolan-5-yl]-pyrimidin-2-one To a solution of the product from step (g) (90 mg) in pyridine (0.2 mL) was added butyric anhydride (1.0 mL) and the resulting mixture was stirred at ambient temperature for 18 hours. Ice-water was added and the aqueous solution was adjusted to pH 2 with 1N HCl/H$_2$O and extracted with CHCl$_3$ (×3). The combined organic phase was washed with saturated NaHCO$_3$/H$_2$O and brine, dried (Na$_2$SO$_4$) and concentrated in vacuo. The resulting oil was dried in vacuo at 50° C. for 18 hours under a stream of nitrogen to obtain the desired product (100 mg) as a colourless solid: $^1$H NMR (CDCl$_3$): δ0.99 (t, 3H), 1.42 (t, 3H), 1.70 (sextuplet, 2H), 2.42 (t, 2H), 3.23 (d, 1H), 3.60 (dd, 1H), 4.45 (dd, 1H), 4.50 (quartet, 2H), 4.65 (dd, 1H), 5.40 (m, 1H), 6.30 (m, 1H), 8.15 (d, 1H); MS m/z 347 (M+1, 25%), 159 (100%).

(i) (2R,5S)-4-Ethoxy-5-fluoro-1-[2-(butanoyloxymethyl)-1-3-oxathiolan-5-yl]pyrimidin-2-one To a solution of the product from step (h) (10 mg) in 20% CH$_3$CN/buffer (3.0 mL, 0.05 M, pH 8.0, phosphate) was added PLE (pig liver esterase, 1.5 μL, Sigma) and the mixture was stirred at ambient temperature for 24 hours. The aqueous solution was extracted with hexane (×2) and the combined extracts were dried (Na$_2$SO$_4$) and concentrated in vacuo. HPLC analysis (Chiral Pack AS; EtOH; 1.5 ml/min) of the organic extracts indicated the presence of a single enantiomeric butyrate ester (4 mg). The enantiomeric alcohol was detected in the aqueous phase. Ester: $^1$H NMR (CDCl$_3$): δ0.97 (t, J=7.4 Hz, 3H), 1.42 (t, J=7.0 Hz, 3H), 1.67 (sextuplet, J=7.4 Hz, 2H), 2.40 (t, J=7.4 Hz, 2H), 3.23 (d, J=12.8 Hz, 1H), 3.60 (dd, J=12.8, 5.3 Hz, 1H), 4.46 (dd, J=12.6, 2.5 Hz, 1H), 4.52 (quartet, J=7.0 Hz, 2H), 4.65 (dd, J=12.6, 4.0 Hz, 1H), 5.37 (m, 1H), 6.29 (m, 1H), 8.12 (d,J=6Hz, 1H).

(j) (2R,5S)-5-Fluoro-1-[2-(hydroxymethyl)-1,3-oxathiolan-5-yl]cytosine

A solution of the ester from step (i) (4 mg) in NH$_3$/MeOH (2 mL) was placed in a steel bomb with a teflon liner, sealed and heated at 70° C. for 18 hours. Solvent was evaporated in vacuo to provide the desired product (2 mg) with HPLC, $^1$H NMR and MS properties identical to those of an authentic sample.

EXAMPLE 2

Preparation of (2R,5S)-1-[2-(hydroxymethyl)-1,3-oxathiolan-5-yl]cytosine (a) 2-Chloro-4-ethoxypyrimidine To a solution of 2,4-dichloropyrimidine (Aldrich, 10.0 g, 67.12 mmol) in abs. EtOH (120 mL) at −3° C. under nitrogen atmosphere was slowly added (over 2 hours) 1M NaOEt/EtOH (68 mL, 68 mmol) and the resulting mixture stirred for 1 hour. Solvent was evaporated in vacuo and the residue partitioned between H$_2$O and Et$_2$O. The aqueous phase was extracted with Et$_2$O and the combined organic phase was washed with brine, dried (Na$_2$SO$_4$) and evaporated (water aspirator pump, 35° C.). The resulting residue was filtered and washed with petroleum ether to provide the desired product (8.05 g, 75%) as a yellowish solid: mp 30–31° C. (lit. 35° C.); $^1$H NMR (CDCl$_3$): δ1.40 (t, J=7.2 Hz, 3H), 4.44 (quartet, J=7.2 Hz, 2H), 6.62 (d, J=5.7 Hz, 1H), 8.27 (d, J=5.7 Hz, 1H); MS m/z 161 (M+3, 34%), 159 (M+1, 100%). Anal. Calcd. for C$_6$H$_7$ClN$_2$O: C, 45.44; H, 4.45; N, 17.66; Cl, 22.36. Found: C, 45.32; H, 4.41; N, 17.60; Cl, 22.43.

(b) 2-(2,2-Dimethoxyethoxy)-4-ethoxypyrimidine

To a suspension of 60% NaH/mineral oil (2.55 g, 63.96 mmol) in anhydrous DMF (70 mL) at 0° C. under nitrogen atmosphere was slowly added glycolaldehyde dimethyl acetal (Aldrich, 5.65 g, 53.3 mmol). The mixture was stirred at ambient temperature for 1 hour and then transferred to a solution of the product from step (a) (8.05 g, 50.76 mmol) in anhydrous DMF (70 mL) at −55° C. over 15 minutes. The mixture was allowed to warm to −20° C. over 2 hours and then neutralized with AcOH. Solvent was evaporated in vacuo and the residue partitioned between H$_2$O and CH$_2$Cl$_2$. The aqueous phase was extracted with CH$_2$Cl$_2$ and the combined organic phase was dried (Na$_2$SO$_4$) and evaporated in vacuo. The residue was flash chromatographed (EtOAc/hexanes, 1:4) to give the desired product (7.92 g, 69%) as a colourless oil: $^1$H NMR (CDCl$_3$): δ1.37 (t, J=7.0 Hz, 3H), 3.44 (s, 6H), 4.36–4.43 (m, 4H), 4.78 (t, J=5.0 Hz, 1H), 6.34 (d, J=6.0 Hz, 1H), 8.15 (d, J=6.0 Hz, 1H); MS m/z 229 (M=1, 13%), 197 (100%). Anal Calcd. for C$_{10}$H$_{16}$N$_2$O$_4$: C, 52.62; H, 7.07; N, 12.27. Found: C, 52.45; H, 7.01; N, 12.26.

(c) 2-[(4-Ethoxy-2-pyrimidinyl)oxy]acetaldehyde

A mixture of the product from step (b) (6.0 g, 24.4 mmol) and 90% TFA/H$_2$O (45 ml) was heated at 50° C. for 2 hours. Solvent was evaporated in vacuo and the residue partitioned between CHCl$_3$ and saturated NaHCO$_3$/H$_2$O. The aqueous phase was extracted with CHCl$_3$ (×2) and the combined extracts were dried (Na$_2$SO$_4$), and evaporated in vacuo to give the desired product (4.48 g, 94%) as a colourless oil: $^1$H NMR (CDCl$_3$): δ1.38 (t, J=7.0 Hz, 3H), 4.37 (quartet, J=7.0 Hz, 2H), 4.80 (s, 2H), 6.40 (d, J=6.0 Hz, 1H), 8.15 (d, J=6.0 Hz, 1H), 9.74 (s, 1H); MS m/z 183 (M+1, 100%). Anal. Calcd. for C$_8$H$_{10}$N$_2$O$_3$.0.25 H$_2$O: C, 51.47; H, 5.67; N, 15.01. Found: C, 51.38; H, 5.69; N, 14.76.

(d) 2-{[(4-Ethoxy-2-pyrimidinyl)oxy]methyl}-1,3-oxathiolan-5-ol

A mixture of the product from step (c) (4.0 g, 22.0 mmol) and 1,4-dithiane-2,5-diol (Aldrich, 1.67 g, 11.0 mmol) in anhydrous toluene (80 mL) was heated at 100° C. for 2 hours. The mixture was filtered and the filtrate concentrated and dried in vacuo to give the desired product (6.27 g, 99%) as a waxy pale yellow oil which was used in the next step without further purification (~1:1 diastereomeric ratio by $^1$H NMR spectroscopy). Flash chromatography (EtOAc/hexanes, 2:3) gave analytically pure material as a colourless oil: $^1$H NMR (CDCl$_3$): δ1.37 (t, J=7.0 Hz, 3H), 3.07 (d, J=11.0 Hz, 1H), 3.18 (d, J=2.3 Hz, 1H), 3.26 (dm, J=11.0 Hz, 1H), 4.38–4.58 (m, 3H), 4.85 (dd, J=12.0, 6.0 Hz, 1H), 5.72 (dd, J=6.0, 4.5 Hz, 1H), 5.92 (m, 1H), 6.39 (d, J=6.0 Hz, 1H), 8.15 (d, J=6.0 Hz, 1H); a similar set of signals appeared for the other diastereomer; MS m/z 197 (M-C$_2$H$_5$O, 41%), 133 (100%). Anal. Calcd. for C$_{10}$H$_{14}$N$_2$O$_4$S: C, 46.50; H, 5.46; N, 10.85; S, 12.41. Found: C, 46.40; H, 5.44; N, 10.79; S, 12.49.

(e) 2-{[(4-Ethoxy-2-pyrimidinyl)oxy]methyl}-1,3-oxathiolan-5-yl acetate

A mixture of the product from step (d) (1.0 g, 3.9 mmol), pyridine (0.7 mL, 0.68 g, 8.65 mmol) and Ac$_2$O (2.0 mL, 2.26 g, 21.2 mmol) was stirred at ambient temperature for 1.5 hours. Ice-water was added and the resulting mixture stirred for 15 minutes. The mixture was extracted with EtOAc and the combined extracts washed with saturated NaHCO$_3$/H$_2$O, dried (Na$_2$SO$_4$), evaporated and dried in vacuo to give the desired product (1.15 g, 99%) as an orange oil which was used in the next step without further purification (~2:1 diastereomeric ratio by $^1$H NMR spectroscopy). $^1$H NMR (CDCl$_3$): δ1.40 (t, 3H), 2.05 (s, 3H), 3.08 (d, 1H), 3.27 (dd, 1H), 4.40–4.70 (m, 4H), 5.79 (m, 1H), 6.38 (d, 1H), 6.75 (d, 1H), 8.18 (d, 1H); a similar set of signals appeared for the minor diastereomer; MS m/z 241 (M-OAc, 4%), 141 (100%). Anal. Calcd. for C$_{12}$H$_{16}$N$_2$O$_5$S: C, 47.99; H, 5.37; N, 9.33; S, 10.68. Found: C, 47.88; H, 5.43; N, 9.22; S, 10.60.

(f) (2S*,5R-)-4-Ethoxy-1-[2-(hydroxymethyl)-1,3-oxathiolan-5-yl]pyrimidin-2-one

To a solution of the product from step (e) (0.20 g, 0.66 mmol) in anhydrous CH$_3$CN (12 mL) at 0° C. under nitrogen atmosphere was slowly added stannic chloride (Aldrich, 0.12 mL, 0.27 g, 1.05 mmol). After stirring for 2 hours at 0° C., 1M NaOH/H$_2$O (5.5 ml, 5.5 mmol) was added. After 1 hour at 0° C., the mixture was neutralized with AcOH. Solvent was evaporated in vacuo and the residue partitioned between CHCl$_3$ and water. The aqueous phase was extracted with CHCl$_3$ (×2) and the combined extracts were dried (Na$_2$SO$_4$) and concentrated in vacuo. The residue was flash chromatographed (EtOAc/hexanes, 2:1, then EtOAc) to give the desired product (0.10 g, 60%) as a white solid: mp 117–118° C.; $^1$H NMR (DMSO-d$_6$): δ1.26 (t, J=7.0 Hz, 3H), 3.15 (dd, J=12.0, 3.5 Hz, 1H), 3.51 (dd, J=12.0, 5.5 Hz, 1H), 3.71–3.84 (m, 2H), 4.26 (quartet, J=7.0 Hz, 2H), 5.22 (t, J=4.0 Hz, 1H), 5.40 (t, J=6.0 Hz, 1H), 6.0 (d, J=7.4 Hz, 1H), 6.18 (dd, J=5.5, 3.5 Hz, 1H), 8.25 (d, J=7.4 Hz, 1H); MS m/z 259 (M+1, 4%), 141 (100%). Anal. Calcd. for C$_{10}$H$_{14}$N$_2$O$_4$S: C, 46.50; H, 5.46; N, 10.85; S, 12.41. Found: C, 46.58; H, 5.49; N, 10.84; S, 12.34.

(g) (2S*,5R*)-4-Ethoxy-1-[2-(butanoyloxymethyl)-1,3-oxathiolan-5-yl]pyrimidin-2-one To a solution of the product from step (f) (0.30 g, 1.16 mmol) in pyridine (0.19 mL, 0.18 g, 2.32 mmol) was added butyric anhydride (0.37 mL, 0.36 g, 2.32 mmol) and the resulting mixture was stirred at ambient temperature for 2 hours. Saturated NaHCO$_3$/H$_2$O was added and, after 1 hour, the mixture was extracted with EtOAc (×2) and the combined extracts were dried (Na$_2$SO$_4$), concentrated in vacuo and flash chromatographed (EtOAc/hexanes, 1:1) to give the desired product (0.21 g, 55%) as a yellowish solid: mp 59–61° C.; $^1$H NMR (CDCl$_3$): δ0.96 (t, J=7.4 Hz, 3H), 1.36 (t, J=7.1 Hz, 3H), 1.68 (sextuplet, J=7.4 Hz, 2H), 1.80 (br s, 1H), 2.36 (t, J=7.4 Hz, 2H), 3.14 (dd, J=12.3, 3.5 Hz, 1H), 3.59 (dd, J=12.3, 5.2 Hz, 1H), 4.40 (m, 3H), 4.59 (dd, J=12.3, 5.2 Hz, 1H), 5.36 (dd, J=5.2, 3.4 Hz, 1H), 5.89 (d, J=7.3 Hz, 1H), 6.34 (dd, J=5.2, 3.9 Hz, 1H), 7.91 (d, J=7.3 Hz, 1H); MS m/z 329 (M=1, 11%), 141 (100%). Anal. Calcd. for C$_{14}$H$_{20}$N$_2$O$_5$S: C, 51.21; H, 6.14; N, 8.53; S, 9.76. Found: C, 51.08; H, 6.15; N, 8.39; S, 9.69.

(h) (2R,5S)-4-Ethoxy-1-[2-(butanoyloxymethyl)-1,3-oxathiolan-5-yl]pyrimidin-2-one To a solution of the product from step (g) (10 mg) in 20% CH$_3$CN/buffer (3.0 mL, 0.05 M. pH 8.0, phosphate) is added PLE (pig liver esterase, 1.5 μL, Sigma) and the mixture is stirred at ambient temperature for 24 hours. The aqueous solution is extracted with hexane (×2) and the combined extracts were dried (Na$_2$SO$_4$) and concentrated in vacuo to give the desired product. HPLC analysis of the organic phase indicates the presence of a single enantiomeric butyrate ester: The enantiomeric alcohol is detected in the aqueous phase.

(i) (2R,5S)-1-[2-(hydroxymethyl)-1,3-oxathiolan-5-yl]cytosine

A solution of the ester from step (h) (4 mg) in NH$_3$/MeOH (2 mL) is placed in a steel bomb with a teflon liner, sealed and heated at 70° C. for 18 hours. Solvent is evaporated in vacuo to give the desired product with HPLC, $^1$H NMR and MS properties identical to those of an authentic sample.

EXAMPLE 3

(2S*,5R*)-5-Fluoro-1-[2-(hydroxymethyl)-1,3-oxathiolan-5-yl]cytosine

A solution of the product from step (g) (10 mg) in NH$_3$/MeOH (2 mL of MeOH saturated with NH$_3$ gas at 0° C. for 45 minutes) was placed in a steel bomb with a teflon liner, sealed and heated at 70° C. for 18 hours. Solvent was evaporated in vacuo and acetone added to give the desired product (8.8 mg, 99%) as a white solid: mp 195–196° C.; $^1$H NMR (DMSO-d$_6$): δ3.10 (dd, J=12.0, 4.2 Hz, 1H), 3.40 (dd, J=12.0, 5.3 Hz, 1H), 3.70 (ddd, J=12.0, 5.5, 3.5 Hz, 1H), 3.77 (ddd, J=12.0, 5.5, 3.5 Hz, 1H), 5.16 (t, J=3.5 Hz, 1H), 5.39 (t, J=5.5 Hz, 1H), 6.11 (m, 1H), 7.56 (br s, 1H), 7.80 (br s, 1H), 8.17 (d, J=7.4 Hz, 1H); MS m/z 248 (M+1, 34%), 130 (100%). Anal. Calcd. for C$_8$H$_{10}$FN$_3$O$_3$S: C, 38.86; H, 4.08; N, 17.00; S, 12.97. Found: C, 38.97; H, 4.05; N, 16.96; S, 12.95.

EXAMPLE 4

(2S*,5R*)-1-[2-(hydroxymethyl)-1,3-oxathiolan-5-yl]cytosine

A solution of (2S*,5R*)-4-ethoxy-1-[2-(hydroxymethyl)-1,3-oxathiolan-5-yl]pyrimidin-2-one (0.21g) in ammonia/methanol (8 mL of methanol saturated with ammonia gas at 0° C. for 45 minutes) was placed in a steel bomb with a teflon liner, sealed and heated at 70° C. for 18 hours. Solvent was evaporated in vacuo and the residue subjected to flash chromatography to give the desired product (0.16g, 89%) as a white solid: mp 184–185° C.; $^1$H NMR (DMSO-d$_6$): δ3.00 (dd, J=11.8, 5.0 Hz, 1H), 3.38 (dd, J=11.8, 5.5 Hz, 1H), 3.63–3.80 (m, 2H), 5.15 (t, J=4.5 Hz, 1H), 5.30 (t, J=6.0 Hz, 1H), 5.70 (d, J=7.3 Hz, 1H); 6.18 (t, J=5.0 Hz, 1H), 7.20 (brd, 2H, NH$_2$), 7.79 (d, J=7.3 Hz, 1H); MS m/z 229.8 (M+1, 4%), 112(100%). Anal. Calcd. for C$_8$H$_{11}$N$_3$O$_3$S: C, 41.91; H, 4.84; N, 18.33; S, 13.99. Found: C, 41.97; H, 4.83; N, 18.24; S, 13.93

What is claimed is:

1. A process for the preparation of compounds of formula (I)

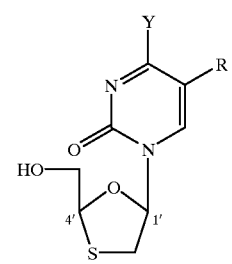

wherein R is hydrogen, C$_{1-6}$ alkyl, or halogen and Y is hydroxy, amino, C$_{1-6}$ alkoxy or OR$^1$, where R$^1$ is a chiral auxiliary; which process comprises treating a compound of formula (II)

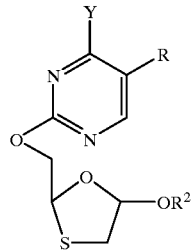
(II)

wherein R and Y are as hereinbefore defined and $R^2$ represents hydrogen, $C_{1-6}$-acyl, $C_{1-6}$-alkyl or halogen with a suitable Lewis acid or a reagent apt to convert the group $OR^2$ to a leaving group followed by treating with an aqueous base.

2. A process according to claim 1 wherein the Lewis acid is stannic chloride or trimethylsilyl triflate.

3. A process according to claim 2 wherein the Lewis acid is stannic chloride and the treatment is carried out at reduced temperature in a polar aprotic solvent.

4. A process according to claim 1 wherein the compound of formula (II) is prepared by reacting a compound of formula (III)

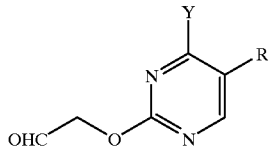
(III)

wherein R is hydrogen, $C_{1-6}$ alkyl, or halogen, and Y is hydroxy, amino, $C_{1-6}$ alkoxy, or $OR^1$ where $R^1$ is a chiral auxiliary, with 1,4-dithiane-2,5-diol and, if necessary or desired, derivatisation.

5. A process according to claim 4 wherein the reaction with 1,4-dithiane-2,5-diol is carried out at elevated temperature in a non-polar aprotic solvent.

6. A process according to claim 5 wherein the reaction with 1,4-dithiane-2,5-diol is carried out at about 100° C. in anhydrous toluene.

7. A method for obtaining a compound of formula (IIa) wherein R is H, $R^2$ is H, $C_{1-6}$ acyl, $C_{1-6}$ alkyl or halogen and Y is $OR^1$ wherein $R^1$ is a chiral auxiliary, from a mixture of isomers by treatment of the mixture of isomers, at least partially in solution, with an agent capable of effecting interconversion of the isomers without complete suppression of the crystallization of the desired single enantiomer (IIa) wherein R is H and Y is $OR^1$.

8. A compound of formula (II)

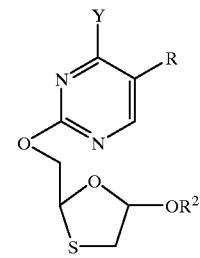
(II)

as defined in claim 1, which compound is selected from the group consisting of 2-{[(4-ethoxy-5-fluoro-2-pyrimidinyl)oxy]methyl}-1,3-oxathiolan-5-ol, 2-{[(4-ethoxy-2-pyrimidinyl)-oxy]methyl}-1,3-oxathiolan-5-ol, 2-{[(4-ethoxy-5-fluoro-2-pyrimidinyl)oxy]methyl}-1,3-oxathiolan-5-yl acetate and 2-{[(4-ethoxy-2-pyrimidinyl)oxy]methyl}-1,3-oxathiolan-5-yl acetate.

9. A compound of formula (IIa)

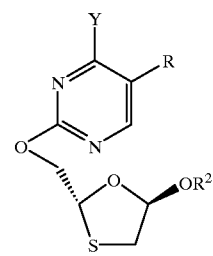
(IIa)

wherein R represents hydrogen, $C_{1-6}$alkyl or halogen, $R^2$ represents hydrogen, $C_{1-6}$acyl, $C_{1-6}$alkyl or halogen and Y represents $OR^1$ wherein $R^1$ represents (d)-menthyl, (l)-menthyl, (d)-8-phenylmenthyl, (l)-8-phenylmenthyl, (+)-norephedrine or (−)-norephedrine.

10. A compound as claimed in claim 9 wherein $R^1$ represents (l)-menthyl.

11. A compound of formula (I)

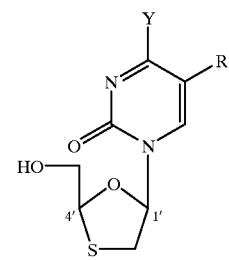
(I)

as defined in claim 1, which compound is selected from (2S*,5R*)-4-ethoxy-5-fluoro-1-[2-(hydroxymethyl)-1,3-oxathiolan-5-yl]pyrimidin-2-one and (2S*,5R*)-4-ethoxy-1-[2-(hydroxymethyl)-1,3-oxathiolan-5-yl]pyrimidin-2-one.

12. A compound selected from the group consisting of (2S*,5R*)-4-ethoxy-5-fluoro-1-[2-(butanoyloxymethyl)-1,3-oxathiolan-5-yl]pyrimidin-2-one and (2S*,5R*)-4-ethoxy-1-[2-(butanoyloxymethyl)-1,3-oxathiolan-5-yl]pyrimidin-2-one.

13. A compound selected from the group consisting of (2S,5R)-4-ethoxy-5-fluoro-1-[2-(hydroxymethyl)-1,3-oxathiolan-5-yl]pyrimidin-2-one and (2S,5R)-4-ethoxy-1-[2-(hydroxymethyl)-1,3-oxathiolan-5-yl]pyrimidin-2-one.

14. A compound selected from the group consisting of (2R,5S)-4-ethoxy-5-fluoro-1-[2-(butanoyloxymethyl)-1,3-oxathiolan-5-yl]pyrimidin-2-one and (2R,5S)-4-ethoxy-1-[2-(butanoyloxymethyl)-1,3-oxathiolan-5-yl]pyrimidin-2-one.

15. A process for the preparation of a compound of formula (Ia)

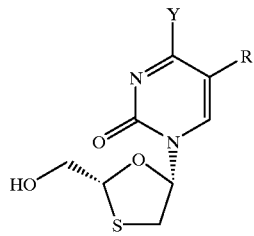

(Ia)

wherein R is hydrogen, $C_{1-6}$ alkyl, or halogen, and Y is hydroxy, amino, $C_{1-6}$ alkoxy or $OR^1$, where $R^1$ is a chiral auxiliary, which process comprises treating a compound of formula (IIa)

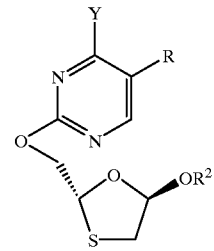

(IIa)

wherein $R^2$ is hydrogen, $C_{1-6}$ acyl, $C_{1-6}$ alkyl or halogen with a suitable Lewis acid or a reagent apt to convert the group $OR^2$ to a leaving group, hydrolyzing the product with an aqueous base and, optionally, where $R^1$ is not a chiral auxiliary esterifying the racemic β-diasteromer, enzymatically hydrolyzing the racemic ester and recovering the desired enantiomer (IIa).

* * * * *

UNITED STATES PATENT AND TRADEMARK OFFICE
CERTIFICATE OF CORRECTION

PATENT NO. : 6,143,748
DATED : November 7, 2000
INVENTOR(S) : Samano et al.

Page 1 of 1

It is certified that error appears in the above-identified patent and that said Letters Patent is hereby corrected as shown below:

Column 4,
Line 44, "enhanced lo greater" should read -- enhanced to greater --

Column 9,
Line 10, "(2S,5R*)" should read -- (2S*, 5R*) --

Column 11,
Line 12, "(2S*5R)" should read -- (2S*, 5R*) --

Signed and Sealed this

Twenty-seventh Day of November, 2001

Attest:

NICHOLAS P. GODICI
Attesting Officer
Acting Director of the United States Patent and Trademark Office